(12) United States Patent
Ward et al.

(10) Patent No.: US 8,921,066 B2
(45) Date of Patent: Dec. 30, 2014

(54) COMPOSITIONS AND METHODS FOR ADHESION OF INTACT CELLS TO AN APPARATUS

(75) Inventors: Christopher Ward, Baltimore, MD (US); William J. Lederer, Baltimore, MD (US); Benjamin L. Prosser, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/196,979

(22) Filed: Aug. 3, 2011

(65) Prior Publication Data

US 2012/0034620 A1     Feb. 9, 2012

Related U.S. Application Data

(60) Provisional application No. 61/370,122, filed on Aug. 3, 2010.

(51) Int. Cl.
*C12Q 1/02*           (2006.01)
*G01N 33/53*        (2006.01)
*C12M 1/12*          (2006.01)

(52) U.S. Cl.
CPC .................................. *C12M 25/00* (2013.01)
USPC ............................................. 435/29; 435/7.1

(58) Field of Classification Search
None
See application file for complete search history.

(56) References Cited

U.S. PATENT DOCUMENTS 6,417,246 B1 *   7/2002   Jia et al. ........................ 523/113
7,285,580 B2 *   10/2007   Stedronsky ................... 523/118

OTHER PUBLICATIONS

Moal et al., Enhanced Fluorescence Cell Imaging with Metal-Coated Slides, Biophysical Journal (92)2150-2161 (2007).*
Life Technologies website offering BSA fluorophore conjugates (http://www.invitrogen.com/site/us/en/home/References/Molecular-Probes-The-Handbook/Fluorescent-Tracers-of-Cell-Morphology-and-Fluid-Flow/Protein-Conjugates.html#head1) (Oct. 7, 2012).*
Wahl and Czernuszka, Collagen-Hydroxyapatite Composites for Hard Tissue Repair, European Cells and Materials, vol. 11, pp. 43-56 (2006).*
Sigma-Aldrich ECM Gel Cell Attachment Protocol, George Sitterley, BioFiles; 3.8, 7, copy provided from the Sigma-Aldrich web site (2008).*
Onohara and Tanaka, Derwent summary of JP 07135961A, published May 30, 1995.*
Schrand et al., Nanodiamond Particles: Properties and Perspectives for Bioapplications, Critical Reviews in Solid State and Material Sciences, 34:18-74 (2009).*
Sigma-Aldrich PDF of Description of Cat. No. E1270, Jul. 2014 (from online catalog, www.sigmaaldrich.com).*
Sugiura, Nishimura, Yasuda, Hosoya, and Katoh, "Carbon fiber technique for the investigation of single-cell mechanics in intact cardiac myocytes", Natural Protocols, 2006; 1: 1453.
Brady, AJ, "Mechanical properties of isolated cardiac myocytes", Physiol. Rev. 1991; 71: 413-28.
Garnier, D, "Attachment procedures for mechanical manipulation of isolated cardiac myocytes: a challenge", Cardiovasc Res. 1994; 28: 1958-64.
Nishimura, Seo, Nagasaki, Hosoya, Yamashita, Fujita, Nagai and Suigiura, "Responses of single-ventricular myocytes to dynamic axial stretching", Biophys and Mol Bio. 2008; 97: 282-97.
Yasuda, Sugiura, Kobayakawa, Fujita, Yamashita, Katoh, Saeki, Kaneko, Suda, Nagai, Sugi, "A novel method to study contraction characteristics of a single cardiac myocytes using carbon fibers", Am. J. Physiol. Heart Circ Physiol. 2001; 281: 3: H1442-H1446).
Bluhm, McCulloch and Lew, "Active force in rabbit ventricular myocytes", J. Bomech. 1995; 28: 1119-1122.
Miyazaki, Hasegawa, Hayashi, "A newly designed tensile tester for cells and its application to fibroblasts", J. Biomech. 2000; 33: 97-104.

* cited by examiner

*Primary Examiner* — Maury Audet
*Assistant Examiner* — Joseph Fischer
(74) *Attorney, Agent, or Firm* — Kristina Castellano; Castellano PLLC

(57) ABSTRACT

Bio-adhesive compositions that include an extra-cellular matrix protein, bovine serum albumin conjugated with a fluorophore, and an aggregate are provided. The bio-adhesive composition may also include at least one component selected from the group consisting of collagen type IV, laminin, and chitosan. Also provided are methods of making the present compositions, that include taking a desired amount of extracellular matrix gel to liquid form of extracellular matrix; adding a desired amount of bovine serum albumin conjugated with a fluorophore; adding a desired amount of aggregate; and mixing. Further provided are methods for attaching cells to an apparatus using the present bio-adhesive compositions, and methods of attaching the present bio-adhesive compositions to an apparatus. Also provided are kits that include the present composition, components thereof or apparatuses, having the present composition attached thereto.

12 Claims, 3 Drawing Sheets

FIG. 1B
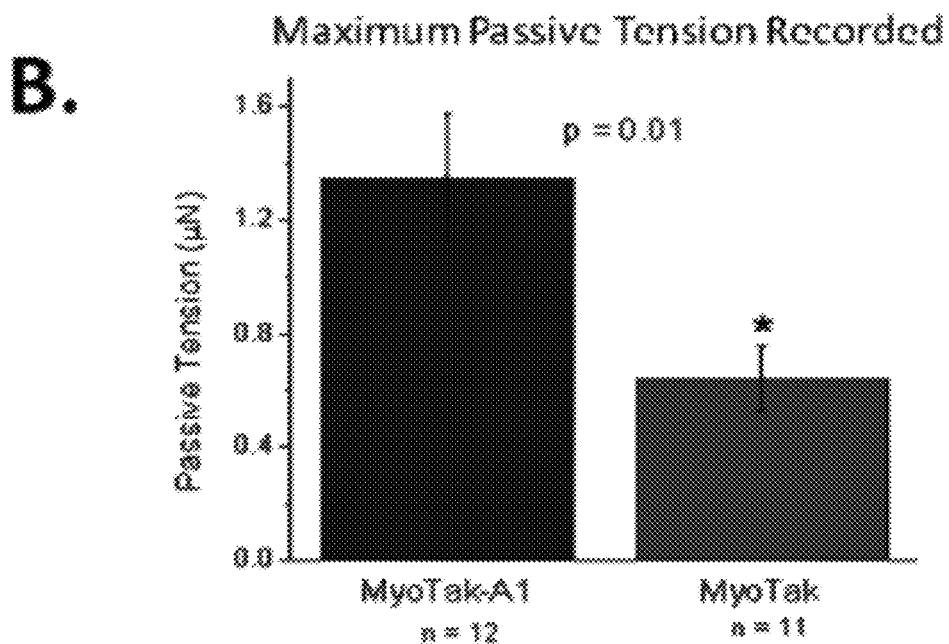
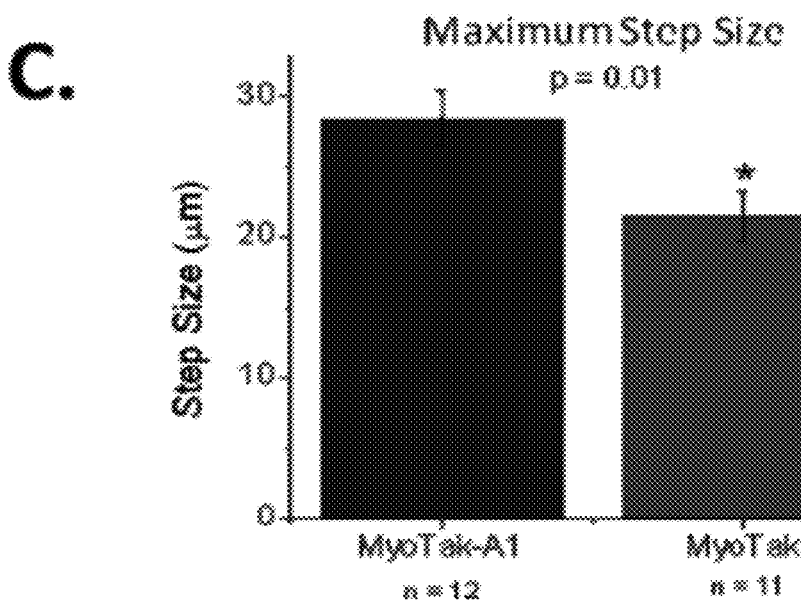
FIG. 1C

COMPOSITIONS AND METHODS FOR ADHESION OF INTACT CELLS TO AN APPARATUS

RELATED APPLICATION

This application claims the benefit of U.S. Provisional Application No. 61/370,122, filed on Aug. 3, 2010, the entire contents of which are hereby incorporated herein in their entirety.

TECHNICAL FIELD

The present invention relates generally to bio-adhesive compositions. The invention also relates to methods of making the present compositions and methods of applying bio-adhesive compositions to an apparatus. The present invention also relates to methods of applying cells, such as intact striated and smooth muscle cells, to an apparatus using the present bio-adhesive compositions. The invention further relates to kits and systems that include one or more of the present compositions.

BACKGROUND

Accurate measurements of cellular mechanical properties are critical to understand a cell's biological response to its environment. The quality of mechanical measurements depends greatly on the attachment method of the apparatus to the cell specimen. The attachment method must provide a strong, reliable connection without altering the integrity of the specimen. Multi-cellular specimens can be attached easily because the exterior cells of the specimen chain can be attached to without fear of damaging the integrity of the interior cells. However, multi-cellular testing presents additional complications, including: 1) heterogeneous electrical activity and stress/strain distributions; 2) the influence of the extracellular matrix on both active and passive properties; and 3) non-uniform orientation of each cell. (Sugiura, Nishimura, Yasuda, Hosoya, and Katoh, "Carbon fiber technique for the investigation of single-cell mechanics in intact cardiac myocytes", *Natural Protocols* 2006; 1: 1453, citing Brady A J, "Mechanical properties of isolated cardiac myocytes", *Physiol. Rev.* 1991; 71: 413-28 and Gamier D, "Attachment procedures for mechanical manipulation of isolated cardiac myocytes: a challenge", *Cardiovasc Res.* 1994; 28: 1958-64). For these reasons, the most accurate measurements can be obtained from single-cell specimens. Single cells do not have any attachment points (e.g., tendons, connective tissue), as with multi-cellular preparations (whole muscles or muscle strip preparations).

Attachment methods for single-cell specimens are much more tedious than those used on multi-cell specimens. There are no available external attachment locations forcing the apparatus to attach directly to the cell membrane. Therefore, the attachment method must not disturb the specimen while still providing strong enough attachment strength to allow for the application of large forces to the specimen. There have been a number of proposed attachment methods including wrapping, glass micro-needles, and suction micropipettes. (Nishimura, Seo, Nagasaki, Hosoya, Yamashita, Fujita, Nagai, and Suigiura, "Responses of single-ventricular myocytes to dynamic axial stretching", *Biophys and Mol Bio.* 2008; 97: 282-97.) Each of these methods is difficult to reproduce and requires extensive technical expertise.

Another known attachment technique uses carbon fibers. Attachment is achieved by gently pressing the tip of the carbon fibers against the cell membrane. (Sugiura et al., citing Brady and Gamier.) This method is also undesirable because the carbon fiber's ability to stick to ventricular myocytes is inconsistent. Also, the method does not provide a reliable attachment point for cellular contractions greater than 2.42 $\mu N$, which is less than the force required to produce large cellular contractions. (Yasuda, Sugiura, Kobayakawa, Fujita, Yamashita, Katoh, Saeki, Kaneko, Suda, Nagai, Sugi, "A novel method to study contraction characteristics of a single cardiac myocytes using carbon fibers", *Am. J. Physiol. Heart Circ Physiol.* 2001; 281: 3: H1442-H1446.) Moreover, the force measurements are dependent upon calculations of the carbon fibers' shortening and compliance which introduces unnecessary variables into the measurement calculations. (Nishimura et al.)

Adhesives have also been used to attach single-cell specimens. Silicon, poly-1-lysine, "Great Stuff" by Dow Chemical, and cyanoacrylate glue are known to have been used. Each of the identified compositions are limiting because a relatively large area of the cell membrane must be glued to achieve proper attachment. In addition, preparation time is extended because the adhesives require an extended amount of time to set and some can only be used on skinned myocytes. (Suigiura et al and Bluhm, McCulloch, and Lew, "Active force in rabbit ventricular myocytes", *J. Bomech.* 1995; 28: 1119-1122.) While cyanoacrylate glue sets quickly and provides a strong grip, exposure will kill the cell in a short period of time, leaving a small window of opportunity to test the specimen.

Other adhesives are available that are specifically marketed for cell adhesion. These include ECM gel from Sigma-Aldrich, Inc. (Sigma-Aldrich, Inc. ECM Gel Product Information Sheet, www.sigma-aldrich.com), Matrigel™ from BD Biosciences, Inc. (BD Matrigel™ Basement Membrane Matrix Product Description, www.bdbiosciences.com), and Cell-Tak™ from BD Biosciences, Inc. (BD Cell-Tak™ Cell and Tissue Adhesive Product Manual. 1991, www.bdbiosciences.com). Matrigel™ and the ECM gel from Sigma-Aldrich are extra-cellular matrices ("ECMs") derived from Engelbreth-Holm-Swarm mouse sarcoma. (BD Matrigel™ Basement Membrane Matrix Product Description, www.bdbiosciences.com). Both are too viscous and allow for specimen movement during mechanical testing. Cell-Tak™ is a bioadhesive derived from the polyphenolic proteins of marine mussels. (BD Cell-Tak™ Cell and Tissue Adhesive Product Manual. 1991, www.bdbiosciences.com) It has been used to attach single-cells extracted from the patellar tendon of matured Japanese white rabbits. (Miyazaki, Hasegawa, Hayashi, "A newly designed tensile tester for cells and its application to fibroblasts", *J. Biomech.* 2000; 33: 97-104) However, during these tests there was approximately a 40% failure rate for the Cell-Tak™ bond. (Miyazaki et al.) Further, no test using the Cell-Tak™ adhesive exceeded a maximum load of 1.1 $\mu N$, which is much less than the load required for testing on myocytes. (Miyazaki et al.)

SUMMARY

There is a need in the art for a reliable method to attach intact single-cell specimens to apparatuses to accurately measure the cellular mechanical properties.

The present inventors have developed novel adhesive compositions and methods of making such compositions. According to non-limiting example embodiments, the present compositions include an extra-cellular matrix protein, bovine serum albumin conjugated with a fluorophore, and an aggregate. Example embodiments of the present invention may contain fluorophores to allow imaging to verify proper application and cell-apparatus adhesion.

The present inventors have also developed novel application methods, for applying cells to an apparatus, which provide for a more reliable and stronger bond to single cell specimens. Non-limiting example embodiments include methods of applying the adhesive composition to an apparatus or support. Further non-limiting example embodiments are directed to novel methods for applying cells to an apparatus e.g., using the present compositions.

Further provided are systems and kits that include one or more of the present compositions and kits that include components for making the present compositions.

BRIEF DESCRIPTION OF DRAWINGS

Non-limiting example embodiments are described herein, with reference to the following accompanying Figures:

FIG. 1 compares data from a test using a bio-adhesive composition without an aggregate (MyoTak®), and using a bio-adhesive composition containing aggregate (MyoTak-A1). FIG. 1B depicts aggregate data from mechanical testing of specimens attached by Myo-Tak without aggregate (MyoTak) versus a specimen attached by Myo-Tak with aggregate (MyoTak-A1). As shown in FIG. 1B and FIG. 1C, the maximum passive tension recorded and the maximum step sizes were both higher for MyoTak-A1.

FIG. 2B shows a single rat ventricular myocyte attached to stiff glass microrods coated with MyoTak®.

DETAILED DESCRIPTION

Figure 1A:
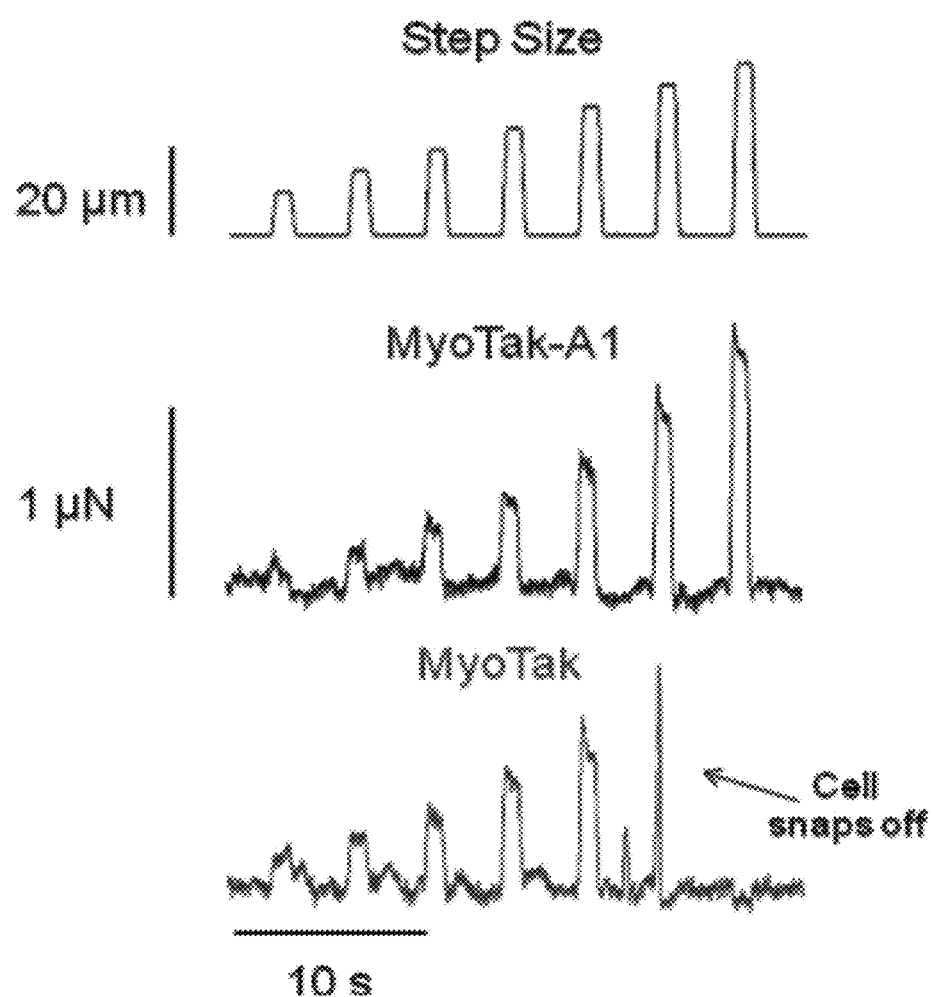
FIG. 1A depicts the results of mechanical testing from a specimen attached by Myo-Tak without aggregate (MyoTak) versus a specimen attached by Myo-Tak with aggregate (Myo-Tak-A1).

According to non-limiting example embodiments, compositions are provided that include an extra-cellular matrix (ECM) protein, bovine serum albumin (BSA) conjugated with a fluorophore, and an aggregate.

Non-limiting example embodiments are also directed to methods of making the present compositions. Such methods may include for example, taking a desired amount of extracellular matrix gel to liquid form of extracellular matrix; adding a desired amount of bovine serum albumin conjugated with a fluorophore; adding a desired amount of aggregate; and mixing.

Non-limiting example embodiments are directed to novel methods to apply the adhesive composition to an apparatus or support. Such methods would advantageously not require extensive technical expertise to perform, are more reliable than available methods, and allow for repeated experiments on a single specimen.

Non-limiting example embodiments also include methods for applying cells to an apparatus. Such methods may include placing a glass coverslip or piece of parafilm under an experimental set-up; pipetting liquid composition onto the coverslip or piece of parafilm; immersing a point of attachment of a measuring apparatus in the composition, such that a portion of the liquid composition attaches to the point of attachment; withdrawing the immersed part of the measuring apparatus from the composition and allowing the coated composition to equilibrate to room temperature. The method may then include attaching a cell sample to the composition-coated point of contact.

Non-limiting example embodiments also include kits that include one or more of the present compositions and optionally instructions for attaching the at least one composition to an apparatus and/or instructions for attaching a cell to an apparatus using the at least one bio-adhesive composition. Example kits may also include one or more components for applying cells to an apparatus, using such compositions, such as the apparatus itself.

Further example embodiments are directed to kits that include components for making the present compositions. For examples, kits may include at least one extracellular matrix, at least one aggregate, and bovine serum albumin conjugated with a fluorophore. Additional components, instructions and/or apparatus' may also be included.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety.

A. DEFINITIONS

In describing example embodiments, specific terminology is employed for the sake of clarity. However, the embodiments are not intended to be limited to this specific terminology. Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Myers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more.

As used herein when used in conjunction with the word "comprising," the words "a" or "an" may mean one or more than one.

As used herein "another" may mean at least a second or more.

As used herein, unless otherwise required by context, singular terms include pluralities and plural terms include the singular.

As used herein, "extracellular matrix," "extracellular matrix proteins," and "extracellular matrices" refer to a matrix composed of a variety of proteins and polysaccharides the major constituents of which are collagens, non-collagenous glycoproteins, and proteoglycans, such as, for example, laminin, collagen type I, collagen type II, collagen type III, collagen type IV, collagen type V, elastin, entactin, fibronectin, tenascin, heparin sulfate, chondroitan sulfate, dermaten sulfate, or karatan sulfate. (Alberts, Johnson, Lewis, Raff, Roberts, Walter, "The Extracellular Matrix of Animals", *Molecular Biology of the Cell*, 4th edition. 2002: Chapter 19). By way of non-limiting example, the extracellular matrix may be an extracellular matrix gel. According to example embodiments, extracellular matrix protein may be derived from Engelbreth Holm-Swarm sarcoma.

As used herein, "Bovine Serum Albumin" or "BSA" refers to the protein serum itself as well as bovine serum albumin conjugated with a fluorophore.

As used herein, "aggregate" refers to any composition added to the bio-adhesive composition which results in an increased stability and a larger surface area for attachment. Known aggregates include alumina silicate or diamond powder, and range from approximately 0.1 µm to 10 µm, or for example from approximately 0.1 µm to 3 µm in diameter depending on the apparatus interface and the type of specimen. The aggregates listed in this application merely serve as examples and do not constitute an exhaustive list. It is believed that non-conductive aggregates will work best.

As used herein, "chitosan" refers to a linear polysaccharide composed of randomly distributed β-(1-4)-linked D-glucosamine (deacetylated unit) and N-acetyl-D-glucosamine (acetylated unit). (Harrison K. Chitosan @ 3Dchem.com. 2009. http://www.3dchem.com/molecules.asp?ID=444). Chitosan is produced commercially by deacetylation of chitin which is the structural element in the exoskeleton of many crustaceans. (Harrison K. Chitosan@3Dchem.com. 2009. http://www.3dchem.com/molecules.asp?ID=444).

As used herein, "apparatus" and "testing apparatus" refer to any measurement system capable of conducting mechanical measurements on single-cell and/or multi-cell specimens.

As used herein, "point of contact" refers to a region of an apparatus to which the cell specimen is attached to the apparatus.

B. COMPOSITIONS

Disclosed herein are bio-adhesive compositions (also simply referred to as "compositions" herein). According to non-limiting example embodiments, compositions are provided that include an extra-cellular matrix protein (ECM), bovine serum albumin (BSA) conjugated with a fluorophore, and an aggregate. A non-limiting, example commercial embodiment of an adhesive composition within the scope of the present invention is termed MyoTak® (for purposes of this application). When the term MyoTak® is used herein, it should be understood that other compositions within the scope of the present invention may be used as well within the scope of the present invention, and such descriptions should not be limited to a particular composition that may be sold or marketed under the name MyoTak®.

According to non-limiting embodiments, compositions provided herein may include an extra-cellular matrix protein, bovine serum albumin conjugated with a fluorophore, an aggregate, and additionally at least one component for increasing bond strength and polymerization. Such components for increasing bond strength and polymerization may include for example, collagen type IV, laminin, and/or chitosan. Accordingly, non-limiting example compositions may include at least one component selected from the group consisting of collagen type IV, laminin, and chitosan.

Extracellular matrix protein(s) in accordance with the present invention may include for example, one or more ECM proteins selected from the list including: laminin, collagen type I, collagen type II, collagen type III, collagen type IV, collagen type V, elastin, entactin, fibronectin, tenascin, heparin sulfate, chondroitan sulfate, karatan sulfate, dermaten sulfate, or a combination thereof. The ECM may be originally provided for example in the form of ECM gel, which may be for example, thawed into a liquid form as described herein, prior forming the present compositions. According to example embodiments, the extra-cellular matrix proteins may be derived from Engelbreth-Holm-Swarm sarcoma.

In non-limiting example embodiments, compositions herein may include extra-cellular matrix protein(s) present in a range of approximately 40-90% by volume as compared to the total composition, aggregate in a range of approximately 10-50% by weight/volume, and bovine serum albumin conjugated with a fluorophore in a range from approximately 5-20% by volume. Collagen type IV, laminin, and/or chitosan may be present in example compositions in a range from approximately 0-45% by volume. A preferred example embodiment may include approximately 65% by volume of extracellular matrix (e.g., ECM gel from Sigma-Aldrich), approximately 30% by weight/volume of alumina silicate 1 µm aggregate, and approximately 5% by volume of bovine serum albumin conjugated with a fluorophore.

The present formulations are unique in that they provide strong bio-adhesive properties and have the ability to attach intact single or multi-cell specimens to an apparatus such that experiments on mechanical properties or length control can be performed without causing any appreciable damage. By way of example striated and/or smooth muscle cells, including single striated and/or smooth muscle cells, may be attached to an apparatus using the present compositions and methods. By way of further example, single cell and/or multi-cell samples of ventricular myocytes may be attached to an apparatus using the present compositions and methods.

Adding aggregate to the ECM increases the surface area for specimen attachment and provides greater stability, allowing for increased test loads. For example, FIG. 1 compares adhesive properties of MyoTak® without aggregate, to MyoTak® with aggregate (MyoTak-A1). As shown in FIG. 1B, Myo-Tak-A1 was able to record higher maximum passive tension and impose a larger step size than MyoTak® alone. Aggregates of various compositions and sizes may be used. For example, alumina silicate and/or diamond powder ranging in size from approximately 0.1 µm to approximately 3.0 µm in diameter. Compositions having similar properties as alumina silicate or diamond powder are believed to make suitable aggregates and are intended to be encompassed by the present application. In addition, aggregate sizes are believed to be effective beyond the range of 0.1 µm to 3.0 µm for example in a range of approximately 0.1 µm to 10.0 µm, and may exceed 10 µm.

The addition of bovine serum albumin in the present composition allows for fluorophore retention within the composition. The flurophore within the composition allows it to be identified and imaged through microscopy when desired. Imaging may be particularly important to verify that the point of contact on the apparatus is properly coated before attaching the specimen. The composition may be conjugated to a flurophore of choice by adjusting the BSA conjugate in the composition. Other matter having similar fluorophore retention properties are believed to likely be effective as well. As indicated above, one or more of collagen type IV, laminin, and/or chitosan may also be added to the composition. Each of these components is believed to increase the bonding strength and the rate of polymerization of the present composition, decreasing the time required to coat the point of contact of the testing apparatus.

The present compositions are versatile and may be used on several commercially available devices used to measure mechanical properties. In addition, the present compositions may be used to attach cells to a substrate to limit mobility. Further, the present compositions may be used for attaching cells to an apparatus or substrate for the purposes of cell body manipulation.

Also provided herein are apparatuses having one or more of the present compositions applied thereto, whether the composition(s) are applied by the present methods (described herein) or by other methods.

C. PREPARATION OF COMPOSITIONS

Non-limiting example embodiments are also directed to methods of making the present compositions. Such methods may include for example, taking a desired amount of extra-cellular matrix gel to liquid form of extracellular matrix; adding a desired amount of bovine serum albumin conjugated with a fluorophore; adding a desired amount of aggregate; and mixing. In example embodiments, the bovine serum albumin may be purchased already conjugated to the fluorophore of choice.

According to non-limiting example embodiments, bovine serum albumin and extracellular matrix may be mixed evenly or substantially evenly prior to adding aggregate. According to other example embodiments, aggregate may be added to ECM prior to adding bovine serum albumin conjugated with a fluorophore.

In embodiments that include a polymerization catalyst, example methods may include adding polymerization catalyst before the aggregate. By way of example, the catalyst may include at least one catalyst selected from the group consisting of collagen IV, laminin, and chitosan.

All components can be mixed for example, by vortex except for some aggregates which must be sonicated to disperse evenly.

Extra-cellular matrix may be provided e.g., in the form of a gel, which is stored frozen. In an example method of preparation a volume of ECM gel may be removed from the freezer and thawed to liquid form, approximately 2 to 8° C., according to certain embodiments approximately 4° C. Bovine serum albumin conjugated with a fluorophore is then added to the liquid form of ECM at approximately 5% volume, and mixed evenly or substantially evenly, e.g., through vortexing the thawed solution. Aggregate of alumina silicate or diamond powder, or a combination thereof, having a diameter size of approximately 0.1 µm to 3.0 µm, may then be added at approximately 20-50% by weight/volume and may be mixed, e.g., vortexed or sonicated, as necessary to disperse evenly or substantially evenly.

In another method of preparation, ECM gel may be removed from the freezer and thawed to liquid form. Bovine serum albumin conjugated with a fluorophore is then added at approximately 5% volume and mixed evenly or substantially evenly e.g., through vortexing the thawed solution. A desired amount of collagen IV, laminin, chitosan, or a combination thereof may then be added and mixed substantially evenly. Aggregate of alumina silicate or diamond powder, or a combination thereof, having a diameter size of approximately 0.1 µm to 3.0 µm, may then be added at approximately 20-50% weight/volume and may be mixed, e.g., vortexed or sonicated, as necessary to disperse evenly or substantially evenly.

In each of the example methods provided herein, when ECM is provided in gel form, so long as the ECM is thawed first, those skilled in the art would understand that certain variations may be made to the order of the steps without affecting the composition. Such variations in the method steps are intended to be encompassed herein.

D. METHODS OF APPLYING COMPOSITIONS TO AN APPARATUS AND METHODS OF APPLYING CELLS TO AN APPARATUS USING THE PRESENT COMPOSITIONS

Non-limiting example embodiments are directed to novel methods to apply an adhesive composition, such as the compositions provided herein, to an apparatus or support. Such methods would advantageously not require extensive technical expertise to perform, are more reliable than available methods, and allow for repeated experiments on a single specimen.

The present compositions (including e.g., MyoTak®) may be a liquid at approximately 4° C. and transform into a gel as they approach room temperature. The present inventors have found that each of the following methods of attachment work best when MyoTak® or other compositions herein, are in liquid form.

One example method to apply the present compositions to an apparatus uses a fine paint brush to brush the composition onto an apparatus point of contact. Another method of applying the present compositions to an apparatus uses a micropipette whereby the drops of the composition are placed on the apparatus point of contact.

A third method of applying the present composition to an apparatus immerses an apparatus point of contact into the composition. An example preferred method of application uses a micropipette to place approximately 1 to 5 µl of Myo-Tak® (or other bioadhesive composition) onto a cover-slip or piece of paraffin film; immersing the apparatus (e.g., glass rods) in the MyoTak® for approximately 1 to 5 minutes; withdrawing the apparatus (e.g., glass rods); and allowing for equalization in the air for approximately 1 to 5 minutes before attaching a specimen to the MyoTak® or other bio-adhesive composition, on the apparatus.

Thus, non-limiting example embodiments include methods for applying cells to an apparatus. A bio-adhesive composition, such as those disclosed herein, may be attached to the apparatus. Then, a cell sample is attached to the composition. Such methods may include for example, placing a glass coverslip or piece of parafilm under an experimental set-up; pipetting liquid composition onto the coverslip or piece of parafilm; immersing a point of attachment of a measuring apparatus in the composition, such that a portion of the liquid composition attaches to the point of attachment; withdrawing the immersed part of the measuring apparatus from the composition and allowing the coated composition to equilibrate to room temperature. The method may then include attaching a cell sample as discussed in other embodiments herein to the composition-coated point of contact.

In yet another method for applying MyoTak® or other compositions to a test apparatus, aggregate which may be approximately 30% w/v, is diluted in approximately 100 µM BSA in water, and is applied to a point of contact of the test apparatus, and is given time to dry. The pre-coated points of contact are then coated with MyoTak® and a cell specimen may be applied using one of the methods previously described.

Non-limiting example embodiments allow for the attached cell(s)/specimen to be used for repeated experiments.

E. KITS

The present compositions and/or components thereof may be included in various kits.

Non-limiting example embodiments include kits that include components for making the present compositions. For examples, kits may include at least one extracellular matrix, at least one aggregate, and bovine serum albumin conjugated with a fluorophore. Non-limiting example kits may further include at least one of collagen type IV, laminen and chitosan.

Example kits may include at least one container in which the bio-adhesive composition may be prepared and/or components for mixing the bio-adhesive composition components into a bio-adhesive composition.

According to example embodiments, kits may include instructions preparing the at least one aggregate, and bovine serum albumin conjugated with a fluorophore (and optionally one or more additional ingredients) into a bio-adhesive composition. Further example kits may include instructions for attaching a composition to an apparatus and/or instructions for attaching cells to an apparatus using the at least one bio-adhesive composition.

Example kits may include one or more components for applying the composition or cells to an apparatus using such compositions, such as the apparatus itself, an apparatus to which a bio-adhesive composition may be bound. For example, the apparatus may include at least one glass micro-rod.

Further example embodiments are directed to kits that include one or more of the present compositions in an already prepared form.

Example embodiments may optionally include instructions for attaching the at least one composition to an apparatus and/or instructions for attaching cells to an apparatus using the at least one bio-adhesive composition.

Example kits may also include one or more components for applying the composition or cells to an apparatus using such compositions, such as the apparatus itself. By way of non-limiting example, the apparatus may include at least one glass micro-rod, which may be included in the kit.

Further example kits may include an apparatus having a bio-adhesive composition already attached thereto. For example, such kits may include an apparatus having MyoTak® applied thereto and dried. Such embodiments may also include instructions for applying cells thereto and/or may include any equipment or additional ingredients that may be used for applying such cells.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

In this example, an embodiment of the present composition is prepared. Extra-cellular matrix gels are stored frozen at approximately −20° C. (Sigma-Aldrich, Inc. ECM Gel Product Information Sheet. www.sigma-aldrich.com). In a method of preparation, a volume of ECM gel (stored in 10-100 μl aliquots) is removed from the freezer and thawed to liquid form, between approximately 2 to 8° C. according to certain embodiments, approximately 4° C. Bovine serum albumin conjugated with a fluorophore is then added to the liquid form of ECM at approximately 5% volume with respect to the BSA or with respect to the final composition, and mixed evenly through vortexing the thawed solution. Aggregate of alumina silicate or diamond powder, or a combination thereof, having a diameter size of approximately 0.1 μm to 3.0 μm, is then added at approximately 20-50% by weight/volume and may be vortexed or sonicated as necessary to disperse substantially evenly.

In another method of preparation, ECM gel is removed from the freezer and thawed to liquid form, between approximately 2 to 8° C., according to certain embodiments, approximately 4° C. Bovine serum albumin conjugated with a fluorophore is then added at approximately 5% volume and mixed evenly e.g., through vortexing the thawed solution. A desired amount of collagen IV, laminin, chitosan, or a combination thereof is added and mixed evenly. Aggregate of alumina silicate or diamond powder, or a combination thereof, having a diameter size of approximately 0.1 μm to 3.0 μm, is then added at approximately 20-50% weight/volume and is vortexed or sonicated as necessary to disperse substantially evenly.

Example 2

The present invention may be used e.g., to improve investigation of single cell function. In this example, single myocytes (such as intact single ventricular myocytes) may be attached to stiff (i.e., non-compliant) glass micro-rods with a biological adhesive according to the present embodiments. In particular, stiff, 25 μm diameter glass micro-rods may be coated with a biological adhesive in accordance with the present invention. The cell may then be subjected to a series of small step like changes in length occurring every few seconds.

By way of Example, MyoTak® may be used as the adhesive composition. MyoTak® is a composition of laminin, entactin, heparin sulfate proteoglycan, gentamicin and Dulbecco's Modified Eagle Medium, collagen IV, Alexa Fluor-647 (a fluorescent label) conjugated to bovine serum albumin (BSA) (Invitrogen) and an inert alumina silica aggregate 1 μm in diameter, dissolved in 100 μM BSA.

Figure 2A:
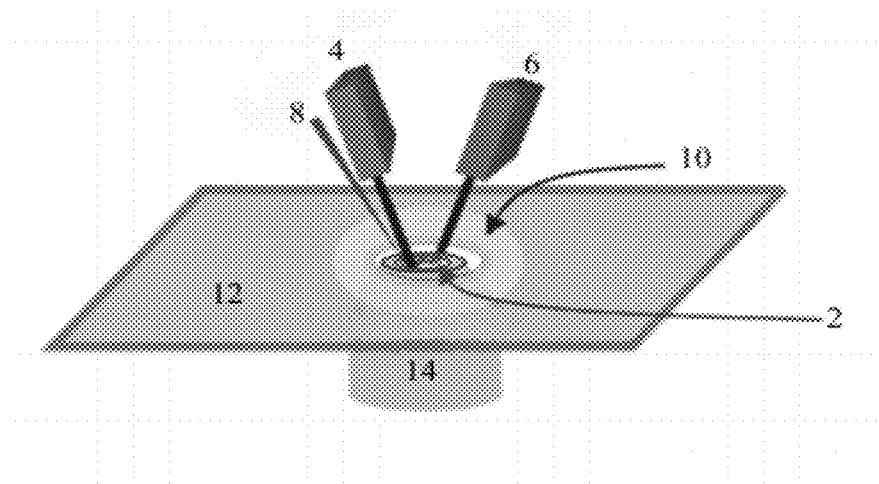
FIG. 2A shows a preferred attachment method setup or testing apparatus, using stiff glass micro-rods as the point of attachment.

As shown in FIG. 2A, a glass micro-rod 2 is connected to a high-sensitivity force transducer 4 (KG7, World Precision Instruments, Sarasota, Fla. (WPI)), and another to a piezo-electric length controller 6 (WPI) driven by a variable voltage output source. The micro-rods 2 are positioned above the cell using motorized micromanipulators (Siskiyou, Grants Pass, Oreg.). Myocytes are attached at both ends by gently pressing down with a MyoTak-coated micro-rod and then lifting the cell from the bottom of the chamber. The distance between the attachment points may be measured and axial stretch applied by movement of the length controller to generate a stretch of attached-cell length. The tension signal from the force transducer and positional output from the length controller may be recorded at 0.5 kHz with an analogue-to-digital recording system. Transmitted light images may be taken before and during stretch and analyzed offline using ImageJ software (NIH) to assay changes in sarcomere length. Myocytes may be typically subjected to 3 stretch-release paradigms lasting 30 s, with 30 s rest allowed between stretches. As each stretch produced a similar change in $Ca^{2+}$ spark rate and change in passive tension.

If desired, various measurements, analysis and imaging may be made, including e.g., $Ca^{2+}$ spark and wave measurements, DCF measurements, western blotting, immunofluorescence, etc.

The present compositions, devices and methods allow precise control of cell length and the measurement of isometric force, thus permitting one to examine the details of stretch-dependent signal transduction. By way of non-limiting example, examination using such attachment, may be used to determine reactive oxygen species (ROS) production (e.g., stretch-dependent and non-stretched).

For example, certain experiments have revealed that stretch-activated $Ca^{2+}$ sparks are triggered by a mechano-chemo signaling pathway that regulates local production of reactive oxygen species (ROS) in heart cells. (See Prosser et al. "X-ROS Signaling: Rapid Mechano-chemo Transduction in Heart", University of Maryland School of Medicine"). FIG. 2A in particular depicts a novel device to measure force and control length for single cardiac ventricular myocytes. The force transducer 4, length controller 6, and patch clamp electrode 8 are shown in position around the cell. The rotating rapid change cell bath 10 is represented by a ring. There is a "stage cradle" 12 that is used to hold all of the devices and the three micromanipulators (not shown for clarity). Below the stage cradle is the high NA 63× water immersion lens 14 that is connected to a microscope. The system also includes diverse perfusion components and platinum stimulation electrodes (not shown).

Figure 2B:
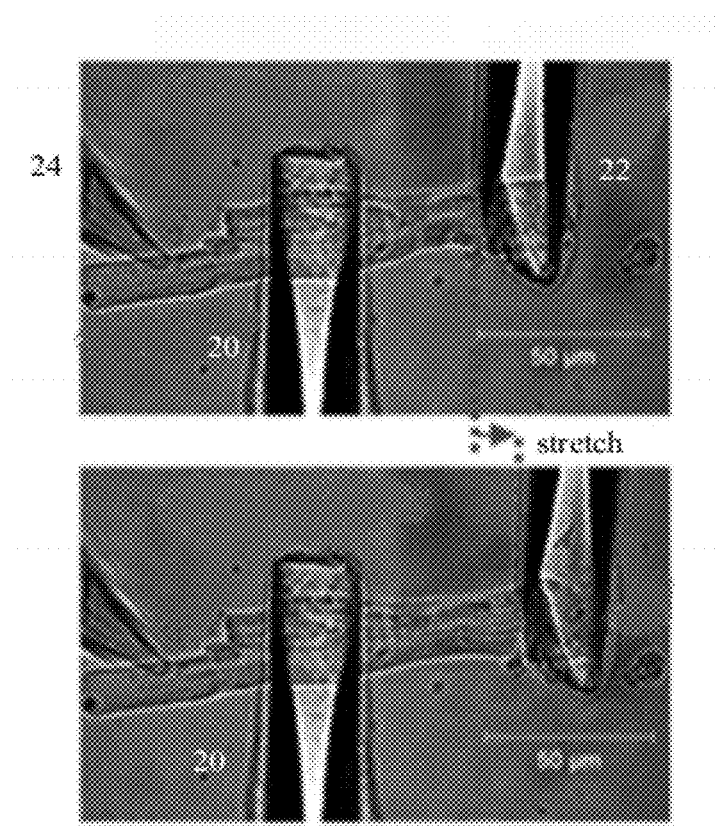
FIG. 2B shows cell specimen deformation during a stretch test using the setup of FIG. 2A. In particular

FIG. 2B shows a half cell stretch protocol. Stiff 20 μm glass micro-rods 20 are attached to a cell with MyoTac-547 that fluoresces when illuminated with 633 nm light. The adhesive connection between micro-rod and cell is strong and permits the cell to be readily lifted and/or stretched/released by the piezoelectric length controller 22 at one cell end. The force transducer is attached to the cell center and the patch clamp pipette 24 is attached at the more stable free end. The rightward displacement of the length-controlling piezo-drive is shown in the bottom portion of FIG. 2B.

The entire system can be moved to a confocal microscope, including ultra-high speed and multiphoton systems. In addition, laser flash photolysis can be used with this system, which also accommodates a temperature-controlled rapid perfusion bath. Hence the novel system provides unprecedented control and quantitation of a multitude of cellular signaling and mechanical transduction pathways.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto

What is claimed is:

1. An intact single cell specimen bio-adhesive composition comprising:
   a solution comprising approximately 65% by volume of liquid extracellular matrix proteins in liquid form, and approximately 5% by volume of bovine serum albumin conjugated with a fluorophore, and
   an aggregate comprising alumina silicate or diamond powder, wherein said aggregate is present in amount of approximately 30% by weight per volume of said total solution said composition for adhesion of an intact single cell to an apparatus.

2. The composition of claim 1, further comprising at least one component selected from the group consisting of collagen type IV, laminin, and chitosan.

3. The composition of claim 1, wherein the extra-cellular matrix protein comprises at least one protein selected from the group consisting of: laminin, collagen type I, collagen type II, collagen type III, collagen type IV, collagen type V, elastin, entactin, fibronectin, tenascin, heparin sulfate, chondroitan sulfate, dermaten sulfate, and karatan sulfate.

4. The composition of claim 1, wherein at least one extracellular matrix protein is derived from Engelbreth-Holm-Swarm sarcoma.

5. The composition of claim 1, wherein the aggregate is approximately 0.1 μm to 3.0 μm in diameter.

6. The composition of claim 1, further comprising at least one ingredient selected from the group consisting of collagen type IV, laminin, and chitosan in an amount up to 45% by volume.

7. A method for making an intact single cell specimen bio-adhesive composition comprising an extra-cellular matrix protein, bovine serum albumin conjugated with a fluorophore, and an aggregate, comprising: thawing a desired amount of extracellular matrix protein gel to approximately 2° C. to 8° C. to a liquid form of extracellular matrix protein;
   adding a desired amount of bovine serum albumin conjugated with a fluorophore;
   adding a desired amount of aggregate comprising alumina silicate or diamond powder; and
   mixing, to form a solution comprising approximately 65% by volume of a liquid extra-cellular matrix protein and approximately 5% by volume of bovine serum albumin conjugated with a fluorophore; and an aggregate comprising alumina silicate or diamond powder, wherein said aggregate is present in amount of approximately 30% weight per volume of said total solution said composition for adhesion of an intact single cell to an apparatus.

8. The method of claim 7, wherein bovine serum albumin and extracellular matrix are mixed substantially evenly prior to adding the aggregate.

9. The method of claim 7, wherein the aggregate is added prior to adding bovine serum albumin conjugated with a fluorophore.

10. The method of claim 7, further comprising adding a polymerization catalyst before the aggregate, wherein the polymerization catalyst comprises at least one catalyst selected from the group consisting of collagen IV, laminin, and chitosan.

11. The method of claim 7, wherein the aggregates are approximately 0.1 μm to 3 μm in diameter.

12. The method of claim 7, wherein taking extracellular matrix gel to liquid form comprises thawing the ECM gel to approximately 4° C.

* * * * *